(12) United States Patent
Naruse et al.

(10) Patent No.: US 9,375,422 B2
(45) Date of Patent: *Jun. 28, 2016

(54) FENTANYL-CONTAINING ADHESIVE PREPARATION FOR EXTERNAL USE

(75) Inventors: Mamoru Naruse, Awa (JP); Kenichi Hattori, Tokushima (JP); Kunihiko Matsushita, Takamatsu (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 149 days.

This patent is subject to a terminal disclaimer.

(21) Appl. No.: 13/319,169

(22) PCT Filed: Jul. 21, 2010

(86) PCT No.: PCT/JP2010/062201
§ 371 (c)(1),
(2), (4) Date: Nov. 7, 2011

(87) PCT Pub. No.: WO2011/010645
PCT Pub. Date: Jan. 27, 2011

(65) Prior Publication Data
US 2012/0071511 A1 Mar. 22, 2012

(30) Foreign Application Priority Data
Jul. 24, 2009 (JP) ................................ 2009-173135

(51) Int. Cl.
*A61K 31/4468* (2006.01)
*A61P 25/04* (2006.01)
*A61K 9/70* (2006.01)

(52) U.S. Cl.
CPC ........... *A61K 31/4468* (2013.01); *A61K 9/7053* (2013.01)

(58) Field of Classification Search
None
See application file for complete search history.

(56) References Cited

U.S. PATENT DOCUMENTS

| 2005/0129748 A1 | 6/2005 | Takada et al. | |
| 2008/0038328 A1* | 2/2008 | Higo et al. | 424/448 |
| 2008/0089926 A1* | 4/2008 | Ishima et al. | 424/449 |
| 2009/0074844 A1* | 3/2009 | Nishiura et al. | 424/449 |
| 2010/0322999 A1* | 12/2010 | Matsushita et al. | 424/449 |

FOREIGN PATENT DOCUMENTS

| CN | 1181931 | 5/1998 | |
| EP | 0 827 741 | 3/1998 | |
| JP | 2004-524336 | 8/2004 | |
| JP | 2008-273865 | * 11/2008 | ......... A61K 31/4468 |
| JP | WO2009/096354 | * 8/2009 | ......... A61K 31/4468 |
| JP | 2010-6761 | 1/2010 | |
| JP | 2011-236379 | 11/2011 | |
| WO | 02/074286 | 9/2002 | |
| WO | 03/070228 | 8/2003 | |
| WO | 2009/096354 | 8/2009 | |
| WO | 2009/157586 | 12/2009 | |

OTHER PUBLICATIONS

English translation of the International Preliminary Report on Patentability and Written Opinion dated Feb. 7, 2012.
International Search Report issued Aug. 31, 2010 in International (PCT) Application No. PCT/JP2010/062201.
Office Action issued Oct. 18, 2012, in corresponding Chinese Application No. 201080030199.2 (English translation).

* cited by examiner

*Primary Examiner* — Dennis Heyer
(74) *Attorney, Agent, or Firm* — Wenderoth, Lind & Ponack, L.L.P.

(57) ABSTRACT

Disclosed is a fentanyl-containing adhesive preparation for external use, wherein an adhesive layer is laminated on a supporting body. The adhesive layer contains SIS, a tackifier resin that is composed of a rosin resin and terpene resin, and a softener that is composed of a plybutene and a liquid paraffin. The adhesive layer also contains fentanyl as an active ingredient. The fentanyl-containing adhesive preparation for external use has excellent skin permeation of fentanyl and high preparation stability, without suffering from crystallization of fentanyl during storage.

4 Claims, 2 Drawing Sheets

FENTANYL-CONTAINING ADHESIVE PREPARATION FOR EXTERNAL USE

This application is a U.S. national stage of International Application No. PCT/JP2010/062201 filed Jul. 21, 2010.

TECHNICAL FIELD

The present invention relates to a patch containing fentanyl for external use which is excellent in permeation of fentanyl through the skin for long term and excellent in preparation-stability without suffering from crystallization of the active ingredient during storage.

BACKGROUND ART

Fentanyl and fentanyl citrate are synthetic narcotic analgesics which have been confirmed being about 200 times more potent in analgesic activity than morphine in animal experiments. Nowadays fentanyl-containing reservoir-type and long-acting preparations for percutaneous absorption type are commercially available, for relieving pains due to cancer and said preparations can maintain the blood concentration of fentanyl practically at effective levels for 24 to 72 hours.

However, such reservoir-type and long-acting preparations for percutaneous absorption are disadvantageous in that the drug absorption after application thereof is fairly slow and the blood concentration arrives at an effective level only after 12 to 24 hours following the initial application, so that they cannot produce an immediate analgesic effect, in that because of their being reservoir-type preparations, they have the problem of fluid leakage, and in that they are very strong irritant to the lesion of application due to their containing ethanol.

Attempts have so far been made to produce matrix-type patches for percutaneous absorption as means for solving the above problems. For example, preparations for percutaneous absorption in which an acrylic adhesive is used are commercialized. However, the acrylic adhesive is generally inferior in drug-release, causing a problem: namely, a desired level of drug-release can be attained only by increasing the content of a main drug (Patent Document 1). The increase in the main drug content causes other problems, for example the problem of crystallization of the main drug during storage, and the problem of residual fentanyl in the preparation after application thereof.

On the other hand, while fentanyl-containing patches in which a styrene-isoprene-styrene block copolymer (hereinafter abbreviated as "SIS") is used as a main base (SIS-based preparations) have also been disclosed in Patent Documents 2 and 3, there have not yet been developed any patches which can be stored for long term without causing crystallization and show stable skin adhesiveness and a sufficient main drug release at the application.

[Patent Document 1] Japanese Patent Publication (Tokuhyo) A 2004-524336
[Patent Document 2] WO 2003/070228
[Patent Document 3] Japanese Patent Publication A 2008-273865

DISCLOSURE OF INVENTION

Problem to be Solved by Invention

Accordingly, it is an object of the present invention to provide a patch containing fentanyl for external use which is excellent in permeation of fentanyl through the skin, is stored for long term without suffering from crystallization of the active ingredient and fulfills adhesive requirements.

Means for Solving the Problem

The present inventors made intensive investigations in an attempt to solve the problems mentioned above and, as a result, found that the above-mentioned problems can be solved by using a rosin resin and a terpene resin together as a tackifier resin in a patch for external use prepared by adding fentanyl to an adhesive base consisting of a softener consisting of a styrene-isoprene-styrene block copolymer, a tackifier resin, and a softener consisting of liquid paraffin and polybutene.

Namely the present invention relates to a patch which is prepared by laminating an adhesive layer on a support, and in the patch for external use prepared by adding fentanyl (1 to 15% by weight per total amount of the adhesive layer) to the adhesive layer containing a styrene-isoprene-styrene block copolymer (5 to 50% by weight per total amount of the adhesive layer), a tackifier resin consisting of a rosin resin and a terpene resin (30 to 60% by weight per total amount of the adhesive layer) and a softener consisting of polybutene and liquid paraffin (5 to 40% by weight per total amount of the adhesive layer), relates to a patch containing fentanyl for external use which is characterized in containing a rosin resin (20 to 40% by weight per total amount of the adhesive layer) and a terpene resin (10 to 30% by weight per total amount of the adhesive layer) as a tackifier resin.

When said rosin resin is especially a hydrogenated rosin glycerol ester, it is possible to obtain the external patch wherein the solubility of fentanyl into the preparation, its release-ability and the skin-adhesiveness of the preparation are especially excellent.

By selecting from the range of 0.5:1 to 3:1 the combination ratio between liquid paraffin and polybutene as a softener it is also possible to obtain the external patch which is lower irritant to the skin and is well balanced in the solubility of the active agent.

Effect of Invention

The present invention exerts such an effect as provision of a patch which is excellent in permeation of fentanyl through the skin, is stored for long term without suffering from crystallization of the active ingredient and fulfills adhesive requirements by selecting above mentioned constituents.

BEST MODE FOR CARRYING OUT THE INVENTION

Figure 1:
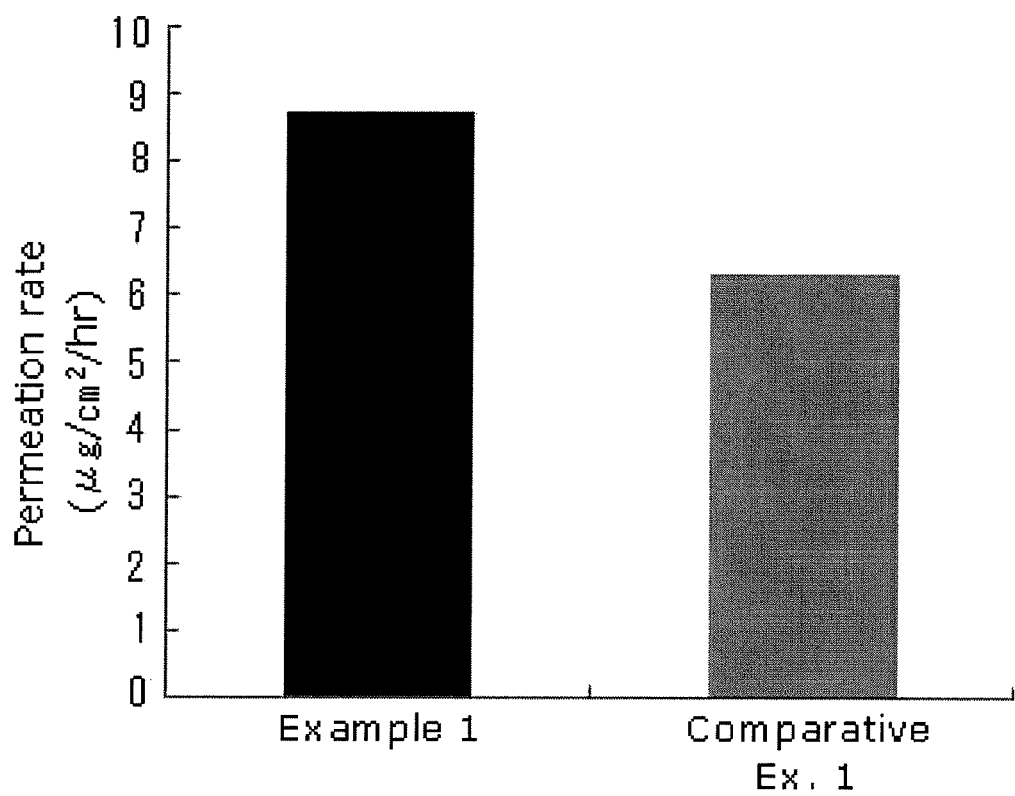
FIG. 1 This figure shows results of skin permeation test on hairless mouse in vitro in Test Example 1.

The amount of SIS used in the external patch of the present invention is 5 to 50% by weight per total amount of the adhesive layer, preferably 10 to 30% by weight per total amount of the adhesive layer.

The tackifier resin gives adhesiveness to the skin by being incorporated in SIS, and its amount is 30 to 60% by weight per total amount of the adhesive layer, more preferably 40 to 55% by weight per total amount of the adhesive layer. When the amount of the tackfier resin is less than 30% by weight, the adhesive property as an external patch becomes bad. When the amount is exceed 60% by weight the adhesive tackiness becomes too strong and when pealing off the patch unfavorably physical stimulation occurs.

Furthermore, the tackifier resin used in the external patch of the present invention is a mixture of a rosin resin and a terpene resin. The rosin resin includes rosin esters, hydrogenated rosins, glycerin rosin esters, hydrogenated rosin glycerol esters, rosin acids, polymerized rosins, and the like; among them hydrogenated rosin glycerol esters are particularly preferred. The amount of the rosin resin is 20 to 40% by weight per total amount of the adhesive layer, more preferably 25 to 35% by weight per total amount of the adhesive layer. When the amount of the rosin resin is 20% by weight or less, the solubility of the drug is decreased and the drug is crystallized and so on to give an unfavorable effect to the physical property of the preparation. When the amount of the rosin resin is 40% by weight or more, the skin permeability of the drug is decreased.

The amount of the terpene resin is 10 to 30% by weight per total amount of the adhesive layer, more preferably 10 to 25% by weight per total amount of the adhesive layer. When the amount of the terpene resin is 10% by weight or less, the skin permeability of the drug is decreased and when the amount is 30% or more, the drug is crystallized and so on to give an unfavorable effect to the physical property of the preparation.

Ratio of the rosin resin and the terpene resin in the present invention is preferably within the range of 4:1 to 1:1, more preferably 3:1.5 to 3:1. When ratio of the rosin resin is beyond 4:1, the skin permeability of the drug is decreased and on the contrary, less than 1:1, the drug is crystallized and so on to give an unfavorable effect to the physical property of the preparation.

The softener is used to improve adaptability to the skin and, further, adjust the tackiness and reduce the physical skin irritation. The softener is selected, in consideration of the solubility of fentanyl and the effects on the physical characteristics of the preparation, and liquid paraffin and polybutene are especially preferable. The amount of it is preferably 5 to 40% by weight, more preferably 10 to 30% by weight. When the amount of the softener is less than 5% by weight, the adhesive agent becomes solid. Therefore adhesiveness itself is rapidly elevated and it causes to skin stimulation and makes adaptability to the skin poor. On the contrary the preparation easily peels off. On the other hand the amount of it is beyond 40% by weight, due to relative decrease of the amount of a rosin resin, crystallization of the drug occurs or adhesive power decreases due to decrease of coagulation power of the adhesive agent and adhesive deposits are unfavorably allowed to remain at the site of application. As for the solubility of fentanyl in liquid paraffin and polybutene, the solubility is higher in polybutene than in liquid paraffin and the solubility of the main drug in the preparation can also be adjusted by the level of addition thereof. Ratio of liquid paraffin and polybutene is preferably 0.5:1 to 3:1, more preferably 1:1 to 2:1. When the proportion of liquid paraffin is higher than 3:1, the solubility of fentanyl in the preparation decreases and such an unfavorable influence as crystallization of the main drug is produced and, further, the adhesiveness of the preparation to the skin decreases. When ratio of the liquid paraffin is lower than 0.5:1, the tackiness becomes excessively strong and the skin irritation becomes strong.

An absorption enhancer and the like may be incorporated in the adhesive layer of the external patch of the present invention in order to promote percutaneous absorption of fentanyl.

The absorption enhancer includes a higher fatty acid ester such as isopropyl myristate or diisopropyl adipate, a higher fatty acid such as isostearic acid, oleic acid or myristic acid, a surfactant such as sorbitan monooleate, polyoxyethylene lauryl ether or monolauric acid polyethylene glycol, and so on.

An antioxidant may be incorporated in the adhesive layer of the external patch of the present invention in order to adjust the stability of the main drug. The antioxidant includes dibutylhydroxy toluene (BHT) or ascorbic acid, preferably BHT. The amount of BHT is 0.1 to 5% by weight, preferably 0.5 to 2% by weight.

In the adhesive layer of the external patch of the present invention if necessary for adjusting the adhesiveness of the base, ingredients which are usually used in preparing the patch are suitably selected. For example water-absorbing polymer such as polyvinylpyrrolidone or polyvinylpyrrolidone/vinyl acetate copolymers, inorganic fillers such as titanium dioxide or silica species and so on are suitably used in suitable amount, if necessary.

Fentanyl is incorporated in the adhesive layer according to the present invention preferably in an amount of 0.1 to 15% by weight, more preferably 1 to 12% by weight, further more preferably 3 to 10% by weight.

The thickness of the adhesive layer according to the present invention is not particularly restricted; however, when the layer is too thin, the adhesive power decreases and, when it is too thick, the amount of the drug remaining unutilized in the preparation increases, the cost increases and the preparation becomes easily peelable upon rubbing against clothing; therefore, the thickness in question is desirably 20 to 100 µm.

Generally, it has been revealed that the flexibility and stretchability of a backing in the patch influence the adaptability to the skin and greatly contribute to improved percutaneous drug absorption. Therefore, the backing having high flexibility and stretchability is used in the patch according to the present invention as well and, as such backing, there may be mentioned a low-density polymer film, a nonwoven fabric, a woven fabric, and the like; from the viewpoints of general versatility and economy, among others, a polyethylene terephthalate film is desirable. Thickness of the film is desirably 0.1 to 100 µm. When the thickness is in excess of 100 µm, the patch can no longer adapt to or follow the unevenness and/or motion of the skin due to the stiffness of the polyethylene terephthalate film, with the result that the percutaneous absorption of the drug decreases.

The release liner used in the present invention includes polyethylene terephthalate, polypropylene, paper, and the like. The release liner is silicone-treated for optimizing the release force, if necessary.

The patch according to the present invention can be prepared, for example, in the following manner.

The base, including the tackifier, is dissolved in an organic solvent, for example toluene, and then agitated and mixed with other ingredients dissolved in an appropriate organic solvent. The obtained solution is applied onto a silicone-treated release liner, followed by 10 minutes of drying at 90° C. to fowl an adhesive layer with a thickness of 20 to 100 µm. The obtained adhesive layer is laminated on a polyethylene terephthalate film, followed by cutting to an appropriate size and shape, whereby the percutaneous absorption preparation according to the present invention can be obtained.

EXAMPLES

The following examples illustrate the present invention more specifically. They, however, by no means limit the scope of the present invention. In the examples, "part(s)" means "part(s) by weight", unless otherwise specified.

Examples 1 to 11

According to the formulations given in Tables 1 and 2, respective patches for external use of Examples were produced.

TABLE 1

| Ingredient | Example 1 | Example 2 | Example 3 | Example 4 | Example 5 |
|---|---|---|---|---|---|
| Styrene-isoprene-styrene block copolymer | 16 | 16 | 16 | 16 | 16 |
| Hydrogenated rosin glycerol ester | 30 | 30 | 30 | 30 | 30 |
| Terpene resin | 20 | 20 | 20 | 20 | 20 |
| Polybutene | 10 | 10 | 10 | 10 | 10 |
| Liquid paraffin | 14.5 | 16 | 17.5 | 14 | 12.5 |
| BHT | 0.5 | 0.5 | 0.5 | 0.5 | 0.5 |
| Monolauric acid polyethylene glycol | | | | 0.5 | |
| Isostearic acid | | | | | 2 |
| Fentanyl | 9 | 7.5 | 6 | 9 | 9 |
| Total | 100 | 100 | 100 | 100 | 100 |

TABLE 2

| Ingredient | Example 6 | Example 7 | Example 8 | Example 9 | Example 10 | Example 11 |
|---|---|---|---|---|---|---|
| Styrene-isoprene-styrene block copolymer | 20 | 20 | 16 | 16 | 16 | 16 |
| Hydrogenated rosin glycerol ester | 30 | 30 | 30 | 30 | 30 | 30 |
| Terpene resin | 30 | 30 | 18 | 18 | 20 | 20 |
| Polybutene | 3 | 8 | 8 | 18 | 10 | 10 |
| Liquid paraffin | 9 | 4 | 20 | 10 | 15.5 | 14.5 |
| BHT | 0.5 | 0.5 | 0.5 | 0.5 | 1.0 | 2.0 |
| Fentanyl | 7.5 | 7.5 | 7.5 | 7.5 | 7.5 | 7.5 |

Comparative Examples 1-9

According to the formulations given in Tables 3 and 4, respective patches for external use of Comparative examples were produced.

TABLE 3

| Ingredient | Comp. ex. 1 | Comp. ex. 2 | Comp. ex. 3 | Comp. ex. 4 | Comp. ex. 5 |
|---|---|---|---|---|---|
| Styrene-isoprene-styrene block copolymer | 16 | 16 | 15 | 25 | 15 |
| Polyisobutylene | | | 10 | | 10 |
| Hydrogenated rosin glycerol ester | 50 | | 15 | 8 | 15 |
| Terpene resin | | 50 | | | |
| Alicyclic petroleum resin | | | 15 | 32 | 15 |
| Polybutene | 10 | 10 | | | |
| Liquid paraffin | 14.5 | 14.5 | 31.5 | 26.5 | 29.5 |
| Ammonium chloride | | | 1 | 1 | 1 |
| Oleyl alcohol | | | 3 | | 3 |
| Dipropylene glycol | | | 2 | | 2 |
| BHT | 0.5 | 0.5 | | | |
| L-Menthol | | | | | 2 |
| Fentanyl | 9 | 9 | 7.5 | 7.5 | 7.5 |
| Total | 100 | 100 | 100 | 100 | 100 |

Comparative example 3: was prepared referring to Example 1 in WO2003/070228.

Comparative example 4: was prepared referring to Example 9 in WO2003/070228.

Comparative example 5: was prepared referring to Example 10 in WO2003/070228.

TABLE 4

| Ingredient | Comp. ex. 6 | Comp. ex. 7 | Comp. ex. 8 | Comp. ex. 9* |
|---|---|---|---|---|
| Styrene-isoprene-styrene block copolymer | 29 | 16 | 28 | 16 |
| Hydrogenated rosin glycerol ester | 30 | 20 | 30 | 20 |
| Terpene resin | 30 | 11 | 30 | 11 |
| Polybutene | 0.5 | 10 | 3 | 35 |
| Liquid paraffin | 2.5 | 35 | 1 | 10 |
| BHT | 0.5 | 0.5 | 0.5 | 0.5 |
| Fentanyl | 7.5 | 7.5 | 7.5 | 7.5 |
| Total | 100 | 100 | 100 | 100 |

*Physical property of Comparative example 9 was too bad to prepare a formulation.

Test 1: Skin Penetration on Hairless Mouse In Vitro

The patches of Examples 1 and Comparative examples 1 were subjected to hairless mouse skin penetration test for fentanyl-release in vitro.

A skin segment excised from the mouse back was set on a Franz cell, the cell was filled with phosphate-buffered saline, and warm water at 37° C. was circulated through the water jacket. A circular sample (16 mm in diameter) was punched out from each preparation and applied to the excised skin, the receptor solution was sampled with time, the amount of fentanyl that had permeated was determined by liquid chromatography, and permeation rate was calculated. The result is shown in FIG. 1.

Test 2: Stability

The preparations of Examples 1 to 9 and Comparative example 1 to 8 after 2 months of storage at room temperature were subjected to appearance observation by visual inspection; the results are shown in Table 5. The preparations showing precipitation of crystal were evaluated as "X" and the preparations showing no precipitation of crystal as "○".

TABLE 5

| | Sample | | | | | | | | |
|---|---|---|---|---|---|---|---|---|---|
| | Ex. 1 | Ex. 2 | Ex. 3 | Ex. 4 | Ex. 5 | Ex. 6 | Ex. 7 | Ex. 8 | Ex. 9 |
| Observation result | ○ | ○ | ○ | ○ | ○ | ○ | ○ | ○ | ○ |

TABLE 5-continued

| Sample | Comp. Ex. 1 | Comp. Ex. 2 | Comp. Ex. 3 | Comp. Ex. 4 |
| --- | --- | --- | --- | --- |
| Observation result | ○ | x | x | x |
| Sample | Comp. Ex. 5 | Comp. Ex. 6 | Comp. Ex. 7 | Comp. Ex. 8 |
| Observation result | ○ | ○ | x | ○ |

Test 3: Adhesiveness

The preparations of Examples 1, 6 to 9, and Comparative examples 3 to 8 were each subjected to 180° peeling-off test using a tensile tester (Rheometer CR500DX, product of Sun Scientific Co., Ltd.) to evaluate the adhesiveness. The results thus obtained are shown in Table 6.

TABLE 6

| Sample | Ex. 1 | Ex. 6 | Ex. 7 | Ex. 8 | Ex. 9 |
| --- | --- | --- | --- | --- | --- |
| Adhesiveness (N) | 6.4 | 8.4 | 9.8 | 3.0 | 3.6 |

| | Sample | | | | | |
| --- | --- | --- | --- | --- | --- | --- |
| | Comp. ex. 3 | Comp. ex. 4 | Comp. ex. 5 | Comp. ex. 6 | Comp. ex. 7 | Comp. ex. 8 |
| Adhesiveness (N) | 0.2 | 1.0 | 0.2 | 13.2 | 0.5 | 13.9 |

Discussion (1) The results shown in Tables 5 to 6 revealed that external patches of the present invention are excellent in drug-release, stability and adhesiveness. On the other hand, it is revealed that the patches of Comparative examples 1 is inferior to the present invention in the main drug-release, patches of Comparative examples 2, 3, 4 and 7 have a trouble in crystallization of the main drug in the preparation and patches of Comparative examples 3 to 5, and 7 are considerably inferior in adhesiveness comparing to the present invention. Furthermore patches of Comparative examples 6 and 8 have much higher adhesiveness comparing with the present invention and therefore it is afraid for skin irritation on them.

Test 4: Rabbit Plasma Concentration

Figure 2:
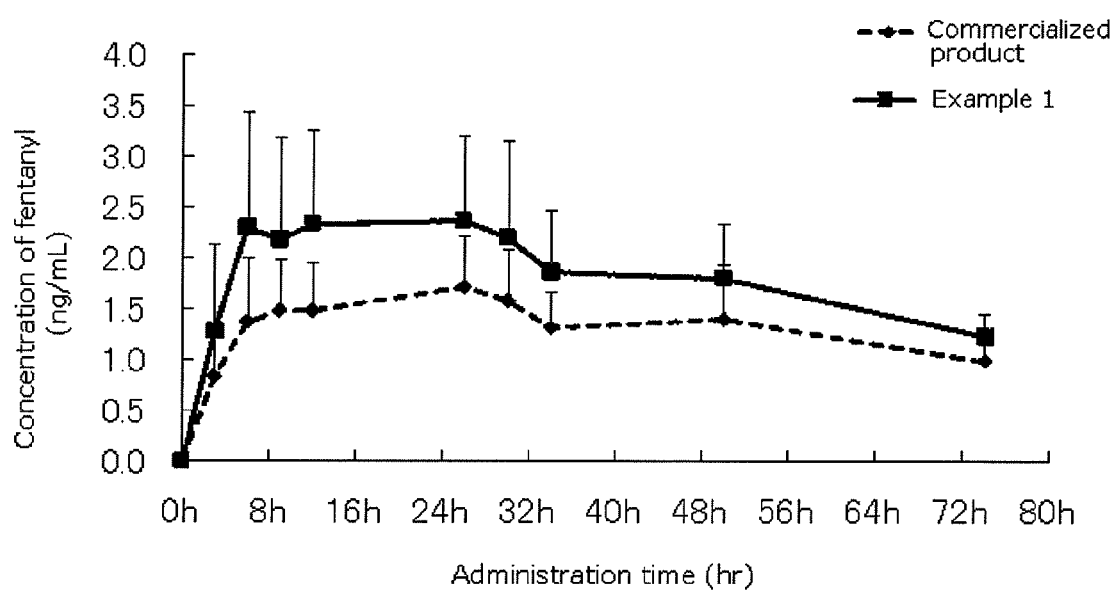
FIG. 2 This figure shows results of plasma concentration assaying on rabbit carried out in Test Example 4.

The patch of Example 1 and a commercialized product (a reservoir-type patch containing fentanyl dissolved in ethanol) were subjected to measurement on rabbit serum concentration of fentanyl (each dose being 4.2 mg). Each patch was applied to the depilated rabbit back for 72 hours, and blood samples were taken with time and subjected to liquid chromatography/mass spectrum method (LC/MS) for plasma fentanyl concentration determination. The results thus obtained are shown in FIG. 2. It was revealed that the patch of the present invention shows quick increase of fentanyl-serum concentration comparing with the commercialized product and maintain higher serum concentration of fentanyl for long term.

INDUSTRIAL APPLICABILITY

The fentanyl-containing patch for external use of the present invention has excellent permeation of fentanyl through the skin for long term, high preparation-stability during storage without suffering crystallization of the active substance, and can be used for relieving pain in cancer patients, and the like.

The invention claimed is:

1. A fentanyl-containing patch for external use prepared by adding fentanyl as an active ingredient to the adhesive layer consisting of
    5 to 50% by weight per total amount of the adhesive layer of a styrene-isoprene-styrene block copolymer,
    30 to 60% by weight per total amount of the adhesive layer of a tackifier resin consisting of a rosin resin and a terpene resin
    and 5 to 40% by weight per total amount of the adhesive layer of a softener consisting of polybutene and liquid paraffin,
wherein the rosin resin and the terpene resin are present in a ratio within the range of 4:1 to 1:1.

2. The fentanyl-containing patch for external use according to claim 1, wherein the amount of the rosin resin is 20 to 40% by weight per total amount of the adhesive layer and the amount of the terpene resin is 10 to 30% by weight per total amount of the adhesive layer.

3. The fentanyl-containing patch for external use according to claim 1, wherein the rosin resin is hydrogenated rosin glycerol ester.

4. A fentanyl-containing patch for external use prepared by adding fentanyl as an active ingredient to an adhesive layer consisting of
    5 to 50% by weight per total amount of the adhesive layer of a styrene-isoprene-styrene block copolymer,
    30 to 60% by weight per total amount of the adhesive layer of a tackifier resin consisting of a rosin resin and a terpene resin,
    5 to 40% by weight per total amount of the adhesive layer of a softener consisting of polybutene and liquid paraffin,
    and, optionally, one or more ingredients selected from the group consisting of one or more absorption enhancers, one or more antioxidants, one or more water-absorbing polymers, and one or more inorganic fillers,
wherein the rosin resin and the terpene resin are present in a ratio within the range of 4:1 to 1:1.

* * * * *